United States Patent [19]

Kleinhappl

[11] Patent Number: 5,715,833
[45] Date of Patent: Feb. 10, 1998

[54] BLOOD SAMPLER

[75] Inventor: Erich Kleinhappl, Schöckelblickstrasse 26, A-8044 Graz, Austria

[73] Assignee: Erich Kleinhappl, Graz, Austria

[21] Appl. No.: 592,801

[22] Filed: Jan. 26, 1996

[30] Foreign Application Priority Data

Feb. 28, 1995 [EP] European Pat. Off. ............... 95890042

[51] Int. Cl.$^6$ ........................................ A61B 5/00
[52] U.S. Cl. ............................ 128/764; 128/763
[58] Field of Search .................... 128/764, 763, 128/762, 760; 604/44, 53, 240

[56] References Cited

U.S. PATENT DOCUMENTS 5,033,476  7/1991  Kasai ..................... 128/764
5,562,639  10/1996  Lynn et al. ................ 604/280

FOREIGN PATENT DOCUMENTS 363169  7/1981  Austria .

*Primary Examiner*—Vincent Millin
*Assistant Examiner*—Robert N. Wieland
*Attorney, Agent, or Firm*—Watson Cole Stevens Davis, P.L.L.C.

[57] ABSTRACT

A blood sampler, especially for drawing samples of arterial blood, is provided with a handle, and a needle adapter to which a puncturing needle is attachable, and a sample capillary connected with the puncturing needle. For robust and cheap manufacture handle and sample capillary are blow-molded to form a single unit and the needle adapter is either molded integral therewith or configured as a separate component, which is insertable into an opening in the handle leading into the sample capillary.

20 Claims, 2 Drawing Sheets

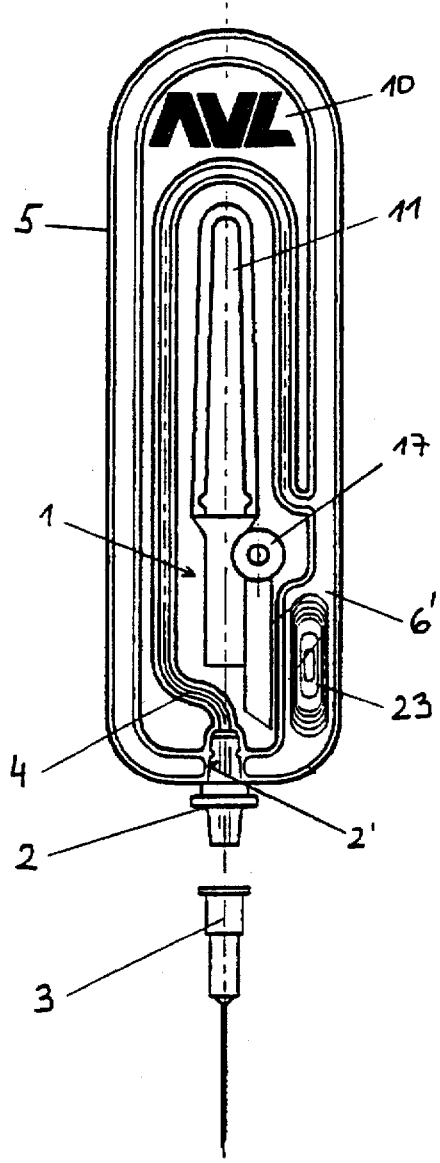
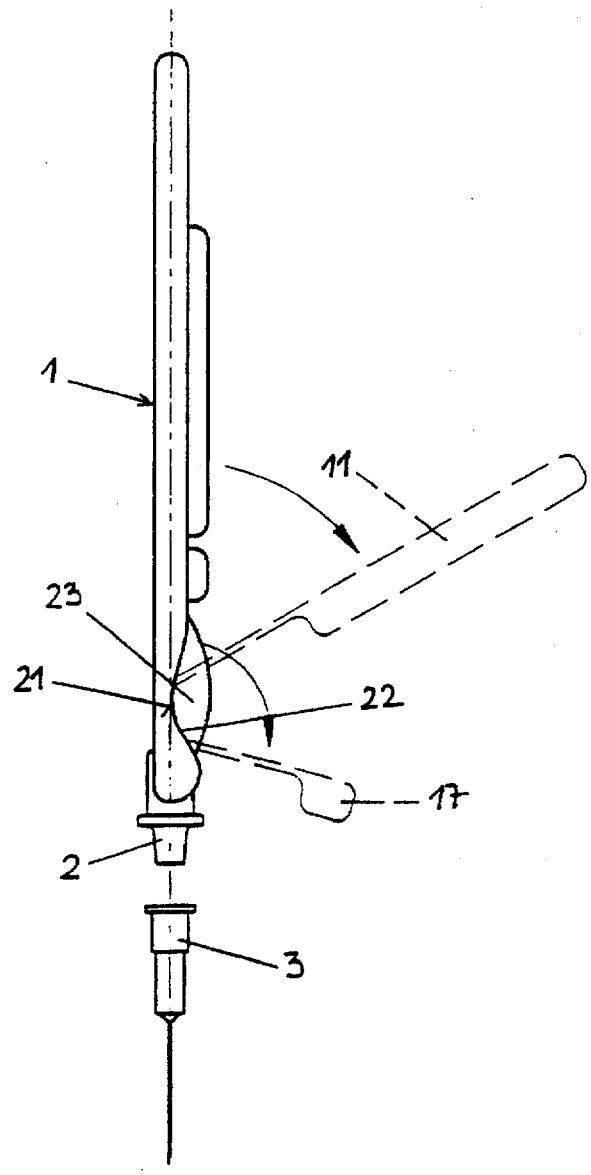
Fig. 5
Fig. 6

BLOOD SAMPLER

BACKGROUND OF THE INVENTION

The invention relates to a blood sampler, especially for drawing samples of arterial blood, with a handle, and a needle adapter to which a puncturing cannula may be attached, and a sample capillary connected with the puncturing cannula, as well as a method for manufacturing such a device.

For purposes of diagnosis, for example, in blood gas analysis, sample withdrawal must take place anaerobically. In this context a number of sampling devices have become known, which are essentially combined of a syringe and a puncturing needle in sterile wrapping. The syringes used for such purposes have a dead space at the front end, which may be filled with an agent for preventing blood clotting, such as heparin.

DESCRIPTION OF THE PRIOR ART

A sampler for which no syringe is required is disclosed in AT-PS 363 169. The sampling unit has a casing which is at least partly transparent and whose closed front wall is provided with a fitting for a puncturing cannula. This fitting has an inlet opening into the interior of the casing, into which a glass capillary may be inserted. The capillary serves as a sample container and is filled due to the arterial blood pressure. The fitting is provided with a protecting cap covering the puncturing cannula, which is removed before the blood is drawn off. The rear end of the casing contains a cover part holding the rear end of the sample capillary. After puncturing, the cover part including the filled capillary may be removed from the casing and inserted into an analyzer, for example. In a variant of the invention the cover part may hold two sample capillaries connected by a U-shaped passage. The only disadvantage of this variant is the relatively large number of individual components, which will lead to an increase in manufacturing cost and handling expenses for assembly and use of the sampler. Another drawback is the danger of leakages due to tolerances of the individual parts to be connected.

Other devices for blood sampling currently on the market exhibit the above deficiencies in addition to poor handling properties, fragile construction (not. suitable for use in pneumatic tube conveyors), or a comparatively high permeability to oxygen and $CO_2$, for instance. For these reasons such devices do not permit unimpaired storage of blood samples for more than a few minutes.

SUMMARY OF THE INVENTION

It is an object of this invention to avoid the drawbacks referred to above and, in particular, to propose a blood sampler of simple and robust construction, which may be manufactured cheaply.

In the invention this is achieved by providing that the handle and sample capillary be blow-molded to form a single unit and that the needle adapter either be molded integral therewith or be configured as a separate component for insertion into an opening in the handle leading into the sample capillary.

According to the invention the blood sampler is blow-molded from a thermoplastic material of tubular shape, essentially in a single piece, the outer contours being obtained with the use of a preferably two-part compression mold, and the lumina of the sample capillary and any other channels by blow-molding. If the needle adapter is molded integral with the body, the fitting surfaces for attachment of the puncturing cannula usually require slight finishing to remove the inevitable flash. If the needle adapter is configured as a separate component made by injection-molding, however, it is permanently locked in an appropriate connecting area of the simple and compact sampler.

In further development of the invention the proposal is put forward that at the end of the sample capillary facing away from the needle adapter an integrally molded reservoir be provided, which should have a vent and serve as an overflow for the sample fluid.

A variant of the invention which is particularly easy to handle is characterized by the fact that the reservoir adjacent to the sample capillary is configured as a small tube and is integrated in a bulged rim of tile. essentially oblong handle.

The device for drawing blood samples, which is referred to as a microsampler, is designed for direct use on the patient. The blood is drawn off by means of a conventional puncturing cannula, which is delivered together with the sampler and is unwrapped and attached just before puncturing. Sterile conditions are required only for the puncturing cannula, whereas the sampler itself need not be sterile under normal conditions of use. The blood sample is pumped into the sampler due to the arterial blood pressure, the unit being vented via a small bore in the bulged rim of the handle. For optimum safety of the patient the sampler is configured as a one-way article which is discarded after use.

By using plastic material of the smallest possible permeability to blood gases such as $O_2$ and $CO_2$, samples for blood gas analysis may be stored in the sampler for up to 30 minutes. It will further be possible to use transparent material for visual checking of the degree of filling of the sample capillary. Suitable materials for this purpose are acrylonitrile methyl acrylate copolymers, PMMA, polycarbonate, polyethylene, and polypropylene.

It is proposed in a variant of the invention that an integrally molded reservoir be provided at the end of the sample capillary facing away from the needle adapter, said reservoir having a finger-deformable area for filling and draining the sample capillary. The advantage of this variant is that a closed system without venting is thus obtained, in which pumping and suction effects are obtained in the sample channel by means of the deformable area in the reservoir.

Without noticeable increase in cost or assembly work it is proposed in an enhanced variant of the invention that the handle of the sampler be provided with a needle protector molded integral therewith, which is attached to the handle by means of an integral turning joint, preferably a film joint, the design of the needle protector permitting the puncturing cannula to be held safely.

A particularly favorable variant provides that a central web area be provided to permit integral molding of the needle protector, which latter is connected to the handle along its circumference by integrally molded breaking sites that are easily ruptured, and, via a flexible connecting piece, by the film joint. The needle protector may thus be automatically molded integral with the unit without further expense. The desired breaking sites are obtained by appropriate design of the tool. After the blood sample has been drawn off the needle protector is folded out by a touch of the finger and drawn over the puncturing cannula. The puncturing cannula locks in an integral groove of the needle protector, the film joint of the protector is broken by a turn of the needle, and the needle may be suitably disposed of together with the protector.

According to the invention a sealing cap may be molded integral with the handle of the sampler, which cap is attached to the handle by an integral joint, preferably a film joint, the design of the cap ensuring a safe seal of the needle adapter. Another web area may be provided for integral molding of the sealing cap whose functional design corresponds to that of the needle protector. After removal of the needle protector the sealing cap is folded out by a touch of the finger and pressed onto the needle adapter. In this way the sample capillary is firmly sealed on the entrance side, preventing any leakage of the blood sample during transport.

Following is a short description of a typical sampling process.

The microsampler is unwrapped from its blister package (each sampler is wrapped individually).

The sterile puncturing cannula delivered together with the sampler is unwrapped.

The puncturing cannula is attached to the Luer cone of the microsampler.

The protecting cap of the puncturing cannula is removed.

The artery is punctured until the required sample volume has been gathered.

The integrated needle protector is tilted out and folded over the needle (protection from injury and contamination).

By turning, both needle protector and puncturing cannula are detached from the microsampler and discarded.

The integrated sealing cap is folded out and pressed onto the Luer cone of the microsampler.

The microsampler is labelled for sample identification.

The microsampler is dispatched to the analyzer (possibly by pneumatic tube).

The sample is fed to into the analyzer directly from the microsampler.

The microsampler may now be discarded.

The sample is analyzed.

It is proposed in an enhanced variant of the invention that further web areas be provided, which should exhibit a surface that is either suitable for hand-written marking of the sampler, i.e. preferably a rough surface, or for attaching labels or machine-readable code tags, i.e. preferably a smooth surface.

The invention finally proposes that the part of the handle adjacent to the needle adapter be provided with a recess for safe gripping of the sampler, by making a dent in the bulged rim. The pressure-deformable reservoir for filling and draining the sample capillary could also be provided in this area.

During manufacture the interior surface of the sampler may be rinsed with a heparin solution. For this purpose the heparin preferably is dissolved in distilled water.

BRIEF DESCRIPTION OF THE DRAWINGS

The invention will now be further described with reference to the accompanying drawings, in which.

DETAILED DESCRIPTION OF PREFERRED EMBODIMENTS

Figure 1:
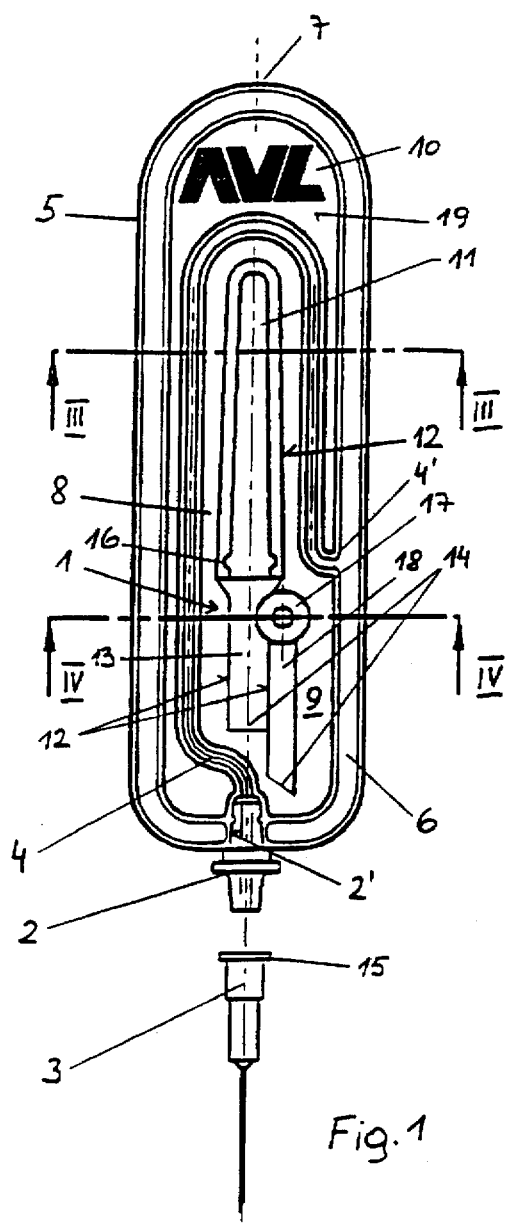
FIG. 1 is a view from above of the sampler of the invention, FIG. 2 a side view.

The sampler presented in FIGS. 1 to 4 approximately in real size has a flat (FIG. 2) striplike handle 1 of rectangular shape, small width and rounded edges, which includes either an integrated needle adapter 2 at one end, or an opening 2' into which a prefabricated needle adapter 2 can be inserted. To this needle adapter 2 a conventional puncturing cannula or sampling needle 3 can be attached, for instance, by means of a Luer connection. All other components of the sampler, which will be described in detail below, are blow-molded in one piece, i.e., in a single working step.

The sampler variant shown here is made of transparent plastic material, its handle 1 being provided with a sample capillary 4 adjacent to the needle adapter 2, which capillary opens into a tubular reservoir 6 forming a bulged rim 5 of the handle 1. At the inlet into the reservoir 6 a constricted passage 4' may be provided. Venting of the sampler is effected via a small bore 7 in the reservoir 6. In this variant the sample capillary 4 and the tubular reservoir 6 are arranged such that a central integral web area 8 and other web areas 9, 10 between sample capillary 4 and reservoir 6 can be used for receiving or providing further integrated components of the sampler.

Figure 2:
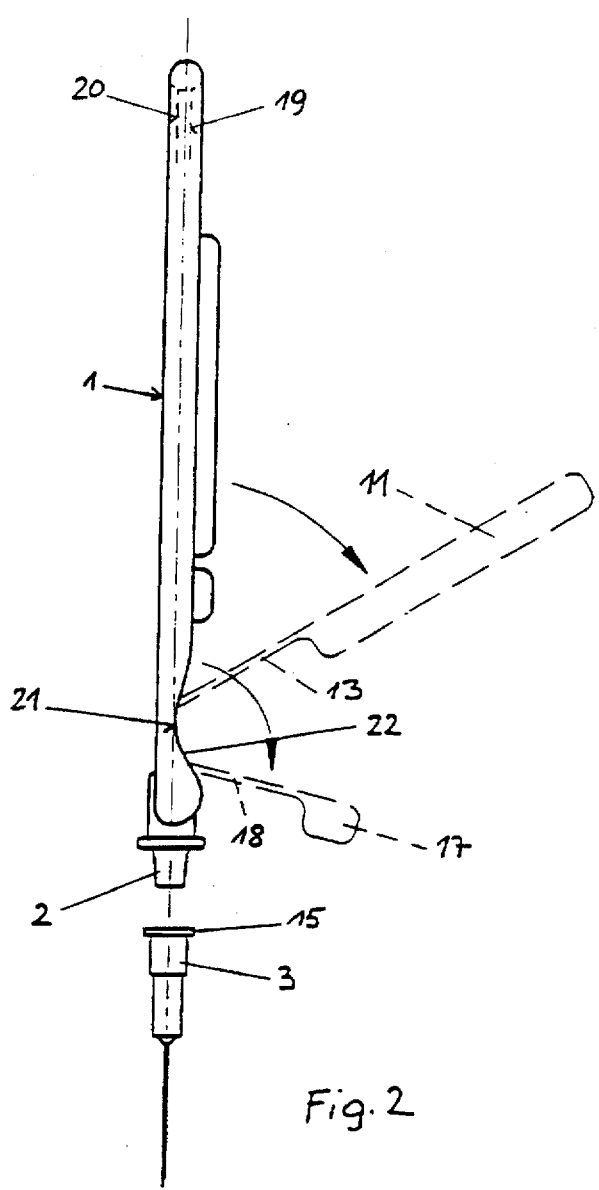

In the central web area 8 an integrated needle protector 11 is provided, which has predetermined breaking sites 12 with the web area 8, enabling it to be tilted out of the handle 1 by a touch of the finger. This position is indicated in FIG. 2 by a broken line. After the sample has been drawn off the needle protector 11 may be folded over the attached puncturing cannula 3 via an integrated flexible connecting piece 13 attached to the handle 1, or rather, web area, by means of a film joint, such that a flange 15 of the Luer connection of the puncturing cannula 3 locks in a groove 16 of the needle protector 11. The needle protector together with the puncturing cannula 3 is turned about the axis of the puncturing cannula such that the film joint 14 is broken and the needle together with the protector can be removed from the sampler and be safely disposed of.

In the same manner an integrally molded sealing cap 17 may be folded out from another web area 9 of the handle, where predetermined breaking sites 12 and a flexible connecting piece 18 are provided, the latter being rotatably connected with the handle 1, or rather, the web area 9, via a further film joint 14. The folded-out sealing cap 17 is represented by a broken line in FIG. 2. With the use of the sealing cap 17 the needle adapter 2 is sealed so as to be gas- and liquid-tight after the sample has been drawn off and the puncturing cannula 3 has been removed. Further web areas 10 within the bulged rim 5 may have a smooth surface 19 to which labels or machine-readable code tags may be attached. The rear surface 20 of the area 10 or additional web areas may have toughened faces which can be written on directly, for example, with a felt tip.

In the part of the handle 1 adjacent to the adapter a dent 21 may be made into the bulged rim 5, thus providing a recess 22 for safe gripping of the sampler.

The volume of the sample capillary 4 is defined by the blow-mold, the wall thickness of the material and the length of the capillary. A typical volume, e.g., for analysing measured values of blood gases and electrolytes, would be 200 μl for modern analyzers. The wall thickness for sample capillary 4, reservoir 6 and web areas 8 to 10 is about 1 to 2 mm, depending on the material used. In various applications length and diameter of the sample capillary may be selected such that a sample volume of 100–500 μl is obtained.

Figure 3:
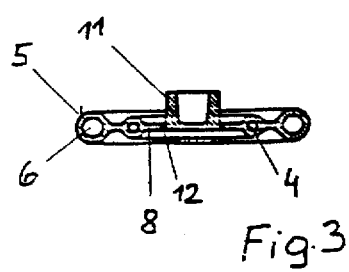
FIGS. 3 and 4 are sections along lines III—III and IV—IV in FIG. 1, and FIGS. 5 and 6 show a variant of the invention in a view from above and from the side, corresponding to the views in FIGS. 1 and 2.
Figure 4:
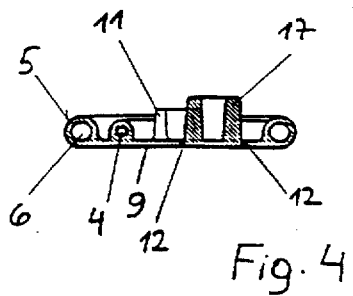

The section of FIG. 3 in the area of the needle protector shows web areas 8 located symmetrically to the reservoir 6 and the sample capillary 4. In a variant according to FIG. 4

(section in the area of the sealing cap 17) the web areas 9 are integrated on one side of the sample capillary 4 and the tubular reservoir 6.

All major components in the variant of FIGS. 5 and 6 are designed in essentially the same manner as in the variant of FIGS. 1 and 2, with the exception of reservoir 6', which is not provided with a vent, but has a finger-deformable area 23 instead, which may be located in the area of the recessed grip 22. By putting pressure on the deformable area 23, or releasing it, a pumping or suction effect is obtained in the sample capillary 4.

The arrangement of the individual components of a blood sampler shown in FIGS. 1 to 6 is to be understood as an example only. The basic concept of the invention does permit other arrangements, provided that the main components of a sampler, such as sample capillary and integrated handle, and possibly the needle adapter and a reservoir, can be manufactured as a single unit by a blow-molding process.

I claim:

1. A blood sampler for drawing samples of blood, with a handle, a needle adapter to which a puncturing cannula is attachable, and a sample capillary connected with said puncturing cannula, wherein said handle and said sample capillary are blow-molded to form a single unit and said needle adapter is either molded integral therewith or configured as a separate component for insertion into an opening in said handle leading into said sample capillary.

2. A blood sampler according to claim 1, wherein at one end of said sample capillary facing away from said needle adapter an integrally molded reservoir is provided, which has a vent and serves as an overflow for said sample of blood.

3. A blood sampler according to claim 2, wherein said reservoir adjacent to the sample capillary is configured as a small tube and is integrated in a bulged rim of an essentially oblong handle.

4. A blood sampler according to claim 1, wherein at one end of said sample capillary facing away from said needle adapter an integrally molded reservoir is provided, which has a finger-deformable area for filling and draining said sample capillary.

5. A blood sampler according to claim 1, wherein said handle is provided with an integrally molded needle protector, which is attached to said handle by means of an integral turning joint, the design of said needle protector permitting said puncturing cannula to be held safely.

6. A blood sampler according to claim 5, wherein said integral turning joint is a film joint.

7. A blood sampler according to claim 5, with a tubular reservoir integrated in a bulged rim of said handle, wherein the longitudinal axes of said tubular reservoir and said sample capillary are situated essentially in the plane of said oblong handle or in a plane parallel thereto, and wherein said handle is essentially constituted by integrally molded web areas.

8. A blood sampler according to claim 1, wherein the handle is provided with an integrally molded sealing cap, which is attached to said handle by an integral turning joint, the design of said sealing cap ensuring a safe seal of said needle adapter.

9. A blood sampler according to claim 8, wherein said integral turning joint is a film joint.

10. A blood sampler according to claim 8, with a tubular reservoir integrated in a bulged rim of said handle, wherein the longitudinal axes of said tubular reservoir and said sample capillary are situated essentially in the plane of said oblong handle or in a plane parallel thereto, and wherein said handle is essentially constituted by integrally molded web areas.

11. A blood sampler according to claim 7, wherein a central web area is provided to permit integral molding of said needle protector, which is connected to said handle along its circumference by integrally molded breaking sites that are easily ruptured, and by a film joint, via a flexible connecting piece.

12. A blood sampler according to claim 7, wherein another web area is provided for integral molding of said sealing cap, which is connected to said handle along its circumference by integrally molded breaking sites that are easily ruptured, and by a film joint, via a flexible connecting piece.

13. A blood sampler according to claim 7, wherein further web areas are provided, which exhibit a preferably rough surface that is suitable for hand-written marking of the sampler.

14. A blood sampler according to claim 7, wherein further web areas are provided which exhibit a preferably smooth surface that is suitable for attaching labels or machine-readable code tags.

15. A blood sampler according to claim 7, wherein a part of said handle adjacent to said needle adapter is provided with a recess for safe gripping of the sampler, by making a dent in said bulged rim.

16. A blood sampler according to claim 1, wherein said sampler is made of plastic material.

17. A blood sampler according to claim 16, wherein at least one material of a group consisting of acrylonitrile methyl acrylate copolymers, PMMA, polycarbonate, polyethylene, and polypropylene.

18. A blood sampler according to claim 1, wherein said sampler is made of transparent material.

19. A method for manufacturing a blood sampler for drawing samples of blood, with a handle, a needle adapter to which a puncturing cannula is attachable, and a sample capillary connected with said puncturing cannula, wherein said sampler is blow-molded from a thermoplastic material of tubular shape, essentially in a single piece, outer contours of said sampler being obtained using a two-part compression mold, and the lumina of said sample capillary and any other channels by blow-molding.

20. A method according to claim 19, wherein the interior surface of said sampler is rinsed with a heparin solution being dissolved in distilled water.

* * * * *